United States Patent
Timinger

(10) Patent No.: US 9,872,631 B2
(45) Date of Patent: Jan. 23, 2018

(54) ARRANGEMENT WITH VARIABLE SELECTION FIELD ORIENTATION FOR MAGNETIC PARTICLE IMAGING

(75) Inventor: Holger Timinger, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1266 days.

(21) Appl. No.: 13/133,236

(22) PCT Filed: Nov. 27, 2009

(86) PCT No.: PCT/IB2009/055386
§ 371 (c)(1),
(2), (4) Date: Jun. 7, 2011

(87) PCT Pub. No.: WO2010/067249
PCT Pub. Date: Jun. 17, 2010

(65) Prior Publication Data
US 2011/0234217 A1   Sep. 29, 2011

(30) Foreign Application Priority Data
Dec. 10, 2008   (EP) .................................... 08171158

(51) Int. Cl.
*A61B 5/05*   (2006.01)
*A61B 8/00*   (2006.01)

(52) U.S. Cl.
CPC .............. *A61B 5/05* (2013.01); *A61B 5/0515* (2013.01); *A61B 8/4494* (2013.01)

(58) Field of Classification Search
USPC .......... 600/407, 408, 409, 410; 324/306–309
See application file for complete search history.

(56) References Cited

U.S. PATENT DOCUMENTS

| | | |
|---|---|---|
| 6,516,213 B1 | 2/2003 | Nevo |
| 6,594,517 B1 | 7/2003 | Nevo |

(Continued)

FOREIGN PATENT DOCUMENTS

| | | |
|---|---|---|
| JP | 2000000310 A | 1/2000 |
| JP | 2009195614 | 9/2009 |

(Continued)

OTHER PUBLICATIONS

By R. G. McNeil et al., Functional Design Featues and Initial Performance Characteristics of a Magnetic-Implant Guidance System for Sterotactic Neurosurgery, IEEE Transactions on Biomedical Engineering, vol. 42, No. 8, Aug. 1995, pp. 793-801.

(Continued)

*Primary Examiner* — Joel F Brutus

(57) ABSTRACT

The present invention relates to an arrangement (10) for influencing and/or detecting magnetic particles (100) in a region of action (300), which comprises selection means (210) for generating a magnetic selection field (211) having a pattern in space of its magnetic field strength such that a first sub-zone (301) having a low magnetic field strength and a second sub-zone (302) having a higher magnetic field strength are formed in the region of action (300). The arrangement further comprises drive means (220) for changing the position in space of the two sub-zones (301, 302) in the region of action (300) by means of a magnetic drive field (221) so that the magnetization of the magnetic material changes locally. The arrangement further comprises receiving means (230) for acquiring detection signals, which detection signals depend on the magnetization in the region of action (300), which magnetization is influenced by the change in the position in space of the first and second sub-zone (301, 302). Control means (76) are further introduced for controlling the selection means (210) to individu- (Continued)

ally set the gradient strength of at least one of the static magnetic gradient fields (211) in a desired direction.

7 Claims, 6 Drawing Sheets

(56) References Cited

U.S. PATENT DOCUMENTS

| | | | |
|---|---|---|---|
| 7,778,681 | B2 | 8/2010 | Gleich |
| 8,183,861 | B2 | 5/2012 | Gleich et al. |
| 2003/0085787 | A1* | 5/2003 | Laskaris ............... H01F 13/003 335/299 |
| 2004/0220468 | A1* | 11/2004 | Watkins et al. ............... 600/410 |
| 2006/0023819 | A1 | 2/2006 | Adkisson et al. |
| 2006/0211939 | A1* | 9/2006 | Gleich ............... 600/410 |
| 2007/0232899 | A1 | 10/2007 | Bill et al. |
| 2010/0072984 | A1 | 3/2010 | Gleich et al. |

FOREIGN PATENT DOCUMENTS

| | | |
|---|---|---|
| WO | 2004091392 A1 | 10/2004 |
| WO | 2004091397 A2 | 10/2004 |
| WO | 2004091721 A1 | 10/2004 |

OTHER PUBLICATIONS

By Y. Bai et al. "Characteristics of an Improved Coil Structure for the Magnetic Stereotaxis System". 2005 IEEE Transactions on Applied Superconductivity; pp. 1-4, please see the abstract, Fig. 1, and section I of the paper; 101109TASC2005849662.pdf.

By J. Weizenecker et al: "Magnetic Particle Imaging Using a Field Free Line", Journal of Physics D. Applied Physics, IOP Publishing, Bristol, GB, vol. 41, No. 10, May 21, 2008 (May 21, 2008), p. 105009 (pp. 1-3), XP020133225 ISSN: 0022-3727 the whole document.

By T.F. Sattel et al: Fast Track Communication; "Single-Sided Device for Magnetic Particle Imaging" Journal of Physics D. Applied Physics, Publishing, Bristol, GB, vol. 42, No. 2, Jan. 21, 2009 (Jan. 21, 2009), p. 22001, XP020149056 ISSN: 0022-3727 the whole document.

By J. Weizenecker et al: "A Simulation Study on the Resolution and Sensitivity of Magnetic Imaging" Physics in Medicine and Biology, Taylor and Francis Ltd. London, GB, vol. 52, No. 21, Nov. 7, 2007 (Nov. 7, 2007), pp. 6363-6374, XP020127229 ISSN: 0031-9155 the whole document.

\* cited by examiner

ARRANGEMENT WITH VARIABLE SELECTION FIELD ORIENTATION FOR MAGNETIC PARTICLE IMAGING

FIELD OF THE INVENTION

The present invention relates to an arrangement for influencing and/or detecting magnetic particles in a region of action.

BACKGROUND OF THE INVENTION

An arrangement of this kind is known from German patent application DE 101 51 778 A1. In the arrangement described in that publication, first of all a magnetic selection field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement has the advantage that it can be used to examine arbitrary examination objects—e.g. human bodies—in a non-destructive manner and without causing any damage and with a high spatial resolution, both close to the surface and remote from the surface of the examination object.

A similar arrangement and method is known from Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication takes advantage of the non-linear magnetization curve of small magnetic particles.

Known arrangements of this type have shown the disadvantage that the imaging resolution is limited due to the above mentioned magnetic selection field which has, due to its physical constraints, an anisotropic gradient strength. Therefore, the spatial selectivity is limited to only one spatial direction, whereas the imaging resolution is significantly weaker for all other spatial directions.

From U.S. Pat. No. 6,594,517 B1 a Magnetic Resonance Imaging (MRI) system is known, including three coils that are orthogonally arranged to each other. By controlling the electrical current through the coils a resultant magnetic dipole interacting with an external field is generated to produce a torque of the desired direction and magnitude.

An adaptation of such a system to MPI systems mentioned above is theoretically possible, but not advantageous since the structure and the arrangement of the coils used in MPI systems significantly differs from MRI systems. Furthermore, the selection field in an MPI system is, in contrast to a MRI system, not dynamic, but a static magnetic gradient field so that the physical principle disclosed in U.S. Pat. No. 6,594,517 B1 cannot be applied and also other physical phenomena occur. In contrast to U.S. Pat. No. 6,594,517 B1, in a MPI system, not the resulting torque is the parameter to be controlled, but instead, the shape and the accurate orientation of the generated selection field itself are the control parameters.

SUMMARY OF THE INVENTION

It is therefore an object of the present invention to provide an arrangement of the kind mentioned initially, wherein the imaging resolution of MPI systems is improved and the spatial selectivity can be adapted according to the desired application.

The object is achieved according to the present invention by an arrangement for influencing and/or detecting magnetic particles in a region of action, comprising:

selection means having three magnetic selection field generation means, one for each main spatial direction, each magnetic selection field generation means generating a selection field component of a static magnetic gradient field having a pattern in space of its magnetic field strength such that a first sub-zone having a low magnetic field strength and a second sub-zone having a higher magnetic field strength are formed in the region of action, drive means for changing the position in space of the two sub-zones in the region of action by means of a magnetic drive field so that the magnetization of the magnetic material changes locally, and control means for controlling the magnetic selection field generation means of said selection means to individually set the gradient strength of the selection field components generated by said magnetic selection field generation means thereby setting the gradient strength and the direction of the gradient of the static magnetic gradient field.

According to the present invention, it is to be understood that the selection means and/or the drive means and/or the receiving means can at least partially be provided in the form of one single coil or solenoid. However, it is preferred according to the present invention that separate coils are provided to form the selection means, the drive means and the receiving means. Furthermore according to the present invention, the selection means and/or the drive means and/or the receiving means can each be composed of separate individual parts, especially separate individual coils or solenoids, provided and/or arranged such that the separate parts form together the selection means and/or the drive means and/or the receiving means. Especially for the drive means and/or the selection means, a plurality of parts, especially pairs for coils (e.g. in a Helmholtz or Anti-Helmholtz configuration) are preferred in order to provide the possibility to generate and/or to detect components of magnetic fields directed in different spatial directions.

With the control means the selection field can, depending on the special application, be directed in a desired spatial orientation. This is in particular advantageous since the magnetic selection field is anisotropic and therefore exhibits a main spatial direction where the gradient strength is stronger than in the all remaining directions. Typically, the gradient is even twice as strong in said main spatial direction. An adaptation of the main spatial direction therefore allows the adaptation of the direction of the highest resolution of the selection field. Thus, it is possible, even though the imaging system is anisotropic, to image most details of the object under examination, just as in a high-resolution isotropic system.

As a result, dependent on the object to be imaged, and the diagnostic scope of the acquired image, the magnetic selection field generates a constant magnetic field gradient, which exhibits its maximum gradient strength along the axis with the most critical structure to be imaged. This ensures maximum resolution along this axis. This is an advantage compared to MPI arrangements of the state of the art, because the spatial orientation with maximum resolution can now be adjusted to the imaging procedure's needs rather than having the maximum resolution along a fixed spatial axis.

In a technical application of the present invention the main spatial direction is therefore adapted to the most critical orientation of the object to be examined in order to receive high-resolution images with the maximum diagnostic benefit. It is to be noted that the main spatial direction can thereby be easily and fast adapted to the different critical object orientations during the examination process. This is especially advantageous since the object under examination, e.g. a human patient, cannot always be repositioned in order to receive a high-resolution image in a desired spatial direction.

According to an embodiment of the present invention, it is preferred that each magnetic selection field generation means comprises a pair of opposed coils provided with identically oriented selection currents wherein the gradient strength of at least one of the selection field components is set by overlaying an overlaid current to at least one of the pairs of coils with the overlaid current of opposed coils being oppositely oriented. If the most critical orientation is, for example, arranged along the principal axis of one of the three coil pairs, the overlaid current is applied to said coil pair in an oppositely oriented direction and therefore the received imaging resolution is twice as large in this specific direction. Thus, it is possible to easily adapt the direction of the highest resolution along the most critical orientation by only overlaying an additional current to the respective coil. It has to be noted that the direction of the highest resolution can be directed to any arbitrary user-defined direction by distributing the overlaid current over these coil pairs which generate the desired spatial fractions of the magnetic selection field. Thus, by providing only three coil pairs, the direction of the highest gradient can be varied to all possible directions within the region of action.

According to another embodiment of the present invention it is proposed that each magnetic selection field generation means comprises a pair of opposed permanent magnets wherein the gradient strength of at least one of the selection field components is set by mechanically moving, in particular rotating, at least one of the pairs of permanent magnets. The mechanical rotation of permanent magnets represents another possibility to realize a variably oriented selection field in which the direction of the highest gradient can be varied to all possible desired directions. In this embodiment, the orientation of the magnetic selection field can be changed rapidly by specific rotation means, e.g. an electro-motor. It is furthermore advantageous that by introducing permanent magnets as magnetic generation means a constant, stable and reproducible magnetic field is realized. It has to noted that the permanent magnets can be of any shape, preferably of a shape such that each permanent magnet optimally contributes to the total magnetic field and the total arrangement is optimally space-saving. This can be realized by spherical permanent magnets which surround the examination region.

In a further preferred embodiment of the present invention, focus means are provided for changing the position in space of the region of action, wherein the focus means and the selection means are realized by the same pairs of coils. Since the operating range of the drive means generating the magnetic field which changes the position in space of the two subzones is limited to the region of action, the introduction of focus means is advantageous since the position in space of the region of action can be changed. The operating range, in which magnetic particles can be influenced and/or detected, is therefore substantially enlarged so that for example longer blood vessels can be easily examined with the arrangement according to the present invention. The direction of the highest resolution can thereby be also varied in a larger area accordingly.

By generating the focus field and the selection field with the same coils or the same permanent magnets a compact and space-saving arrangement is realized. In this embodiment, the combined coils generating both magnetic fields have to be designed in larger dimensions.

It is furthermore preferred according to an embodiment of the present invention that the control means are adapted for controlling the magnetic selection field generation means of said selection means such that the sum of the field strength and the sum of the gradient strength of all three selection field components is maintained at a predefined fixed level. This means that by setting the gradient strength in a desired direction in order to receive the highest possible resolution in said direction, the overall field and/or the overall gradient strength of the selection field is not changed. Thus, a higher resolution is received in the desired direction without depositing additional energy to the examination object. This is especially advantageous in case of human patients so that they are not exposed to additionally energetic radiation, but the imaging resolution is still maintained at a high level independent of the desired direction.

Finally, in an embodiment receiving means are provided for acquiring detection signals, which detection signals depend on the magnetization in the region of action, which magnetization is influenced by the change in the position in space of the first and second sub-zone.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

Figure 1:
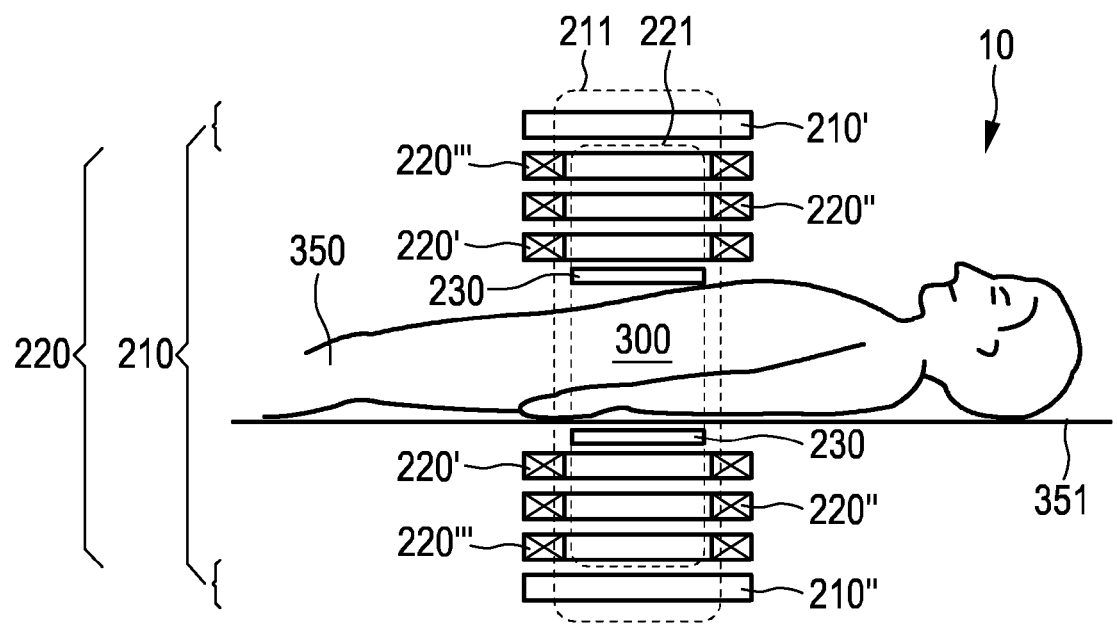
FIG. 1 shows a schematic view of the principle layout of a magnetic particle imaging (MPI) arrangement.

FIG. 1 shows an arbitrary object to be examined by means of a MPI arrangement 10. The reference numeral 350 in FIG.

1 denotes an object, in this case a human or animal patient, who is arranged on a patient table 351, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
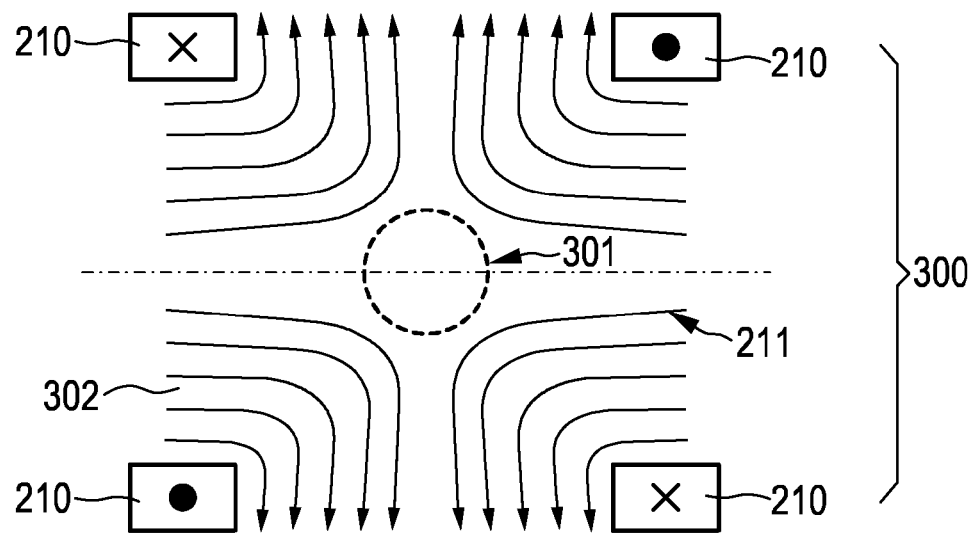
FIG. 2 shows an example of the field line pattern produced by an arrangement according to the present invention.

As an example of an embodiment of the present invention, an arrangement 10 is shown in FIG. 2 comprising a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
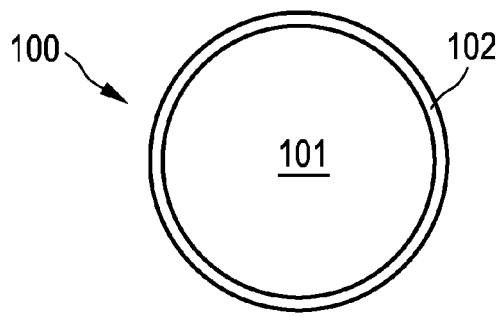
FIG. 3 shows an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to $160 \cdot 10^3$ A/m2, the first sub-zone 301 in which the magnetization of the particles 100 is not saturated has dimensions of about 1 mm (in the given space direction).

When a further magnetic field—in the following called a magnetic drive field 221 is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220''' which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220''' are provided in order to generate components of the magnetic drive field 221 which extend in a different direction in space, e.g. horizontally in the longitudinal direction of the region of action 300 (or the patient 350) and in a direction perpendicular thereto. If third and fourth coil pairs 220", 220''' of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220''' are also arranged above and below the region of action 300 and, therefore, their winding configuration must be different from that of the second coil pair 220'. Coils of this kind, however, are known from the field of magnetic resonance apparatus with open magnets (open MRI) in which an radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement according to the present invention, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
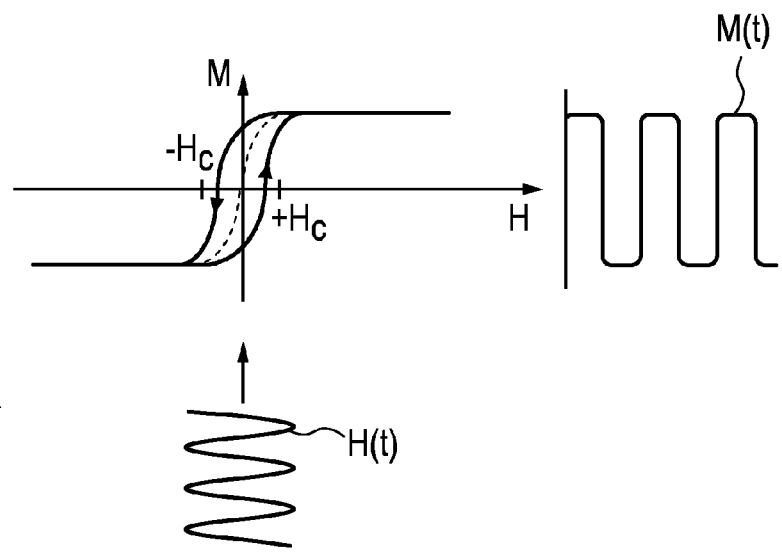
FIGS. 4a and 4b show the magnetization characteristics of such particles.
Figure 4B:
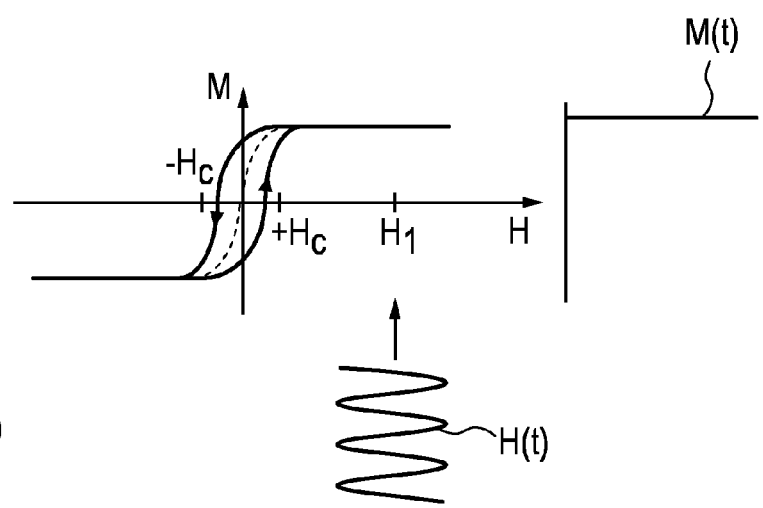

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particeles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
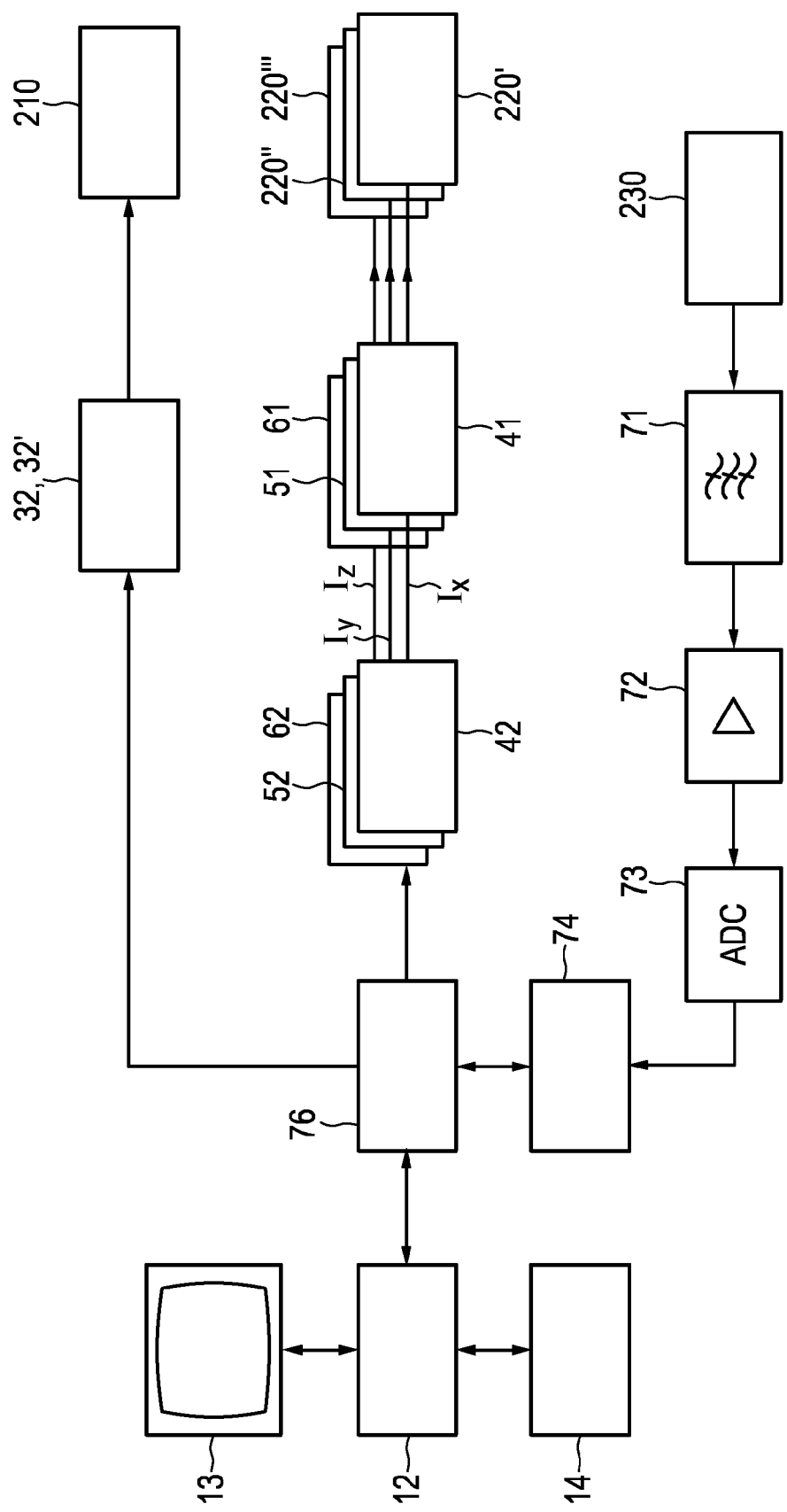
FIG. 5 shows a block diagram of the apparatus according to the present invention.

FIG. 5 shows a block diagram of the apparatus 10 shown in FIG. 1. The selection means 210 is shown schematically in FIG. 5. Preferably, the selection means 210 are provided with three magnetic selection field generation means, in particular either coils, permanent magnets or a combination of coils and permanent magnets. Said three magnetic selection field generation means are preferably arranged such that for each spatial direction one magnetic selection field generation means is provided. If in an embodiment coil pairs are provided as magnetic selection field generation means, the coil pairs are supplied with a DC current from a controllable current source 32, said current source 32 being controlled by the control means 76. In order to individually set the gradient strength of the selection field 211 in a desired direction, an overlaid current is overlaid to at least one of coil pairs, wherein the overlaid current of opposed coils is oppositely oriented. In a preferred embodiment, the control means 76 furthermore controls that the sum of the field strength and the sum of the gradient strength of all three spatial fractions of the selection field 211 is maintained at a predefined level.

If in an embodiment permanent magnets are provided as magnetic selection field generation means instead of coil pairs, the current source 32 need to be exchanged by an actuation means 32', e.g. an electro motor, which is able to mechanically move the permanent magnets in order to set the gradient strength in the desired direction according to the control signals provided by the control means 76.

The control means 76 is in turn connected to a computer 12 which is coupled to a monitor 13 for displaying the distribution of magnetic particles in the examination area and an input unit 14, for example a keyboard. A user is therefore able to set the desired direction of the highest resolution and in turn receives the respective image of the region of action on the monitor 13. If the critical direction, in which the highest resolution is needed, deviates from the direction set first by the user, the user can still vary the direction manually in order to produce a further image with an improved imaging resolution. This resolution improvement process can also be operated automatically by the control means 76 and the computer 12. The control means 76 in this embodiment sets the gradient field in a first direction which is automatically estimated or set as start value by the user. The direction of the gradient field is then varied stepwise until the resolution of the thereby received images, which are compared by the computer 12, is maximal, respectively not improved anymore. The most critical direction can therefore be found respectively adapted automatically in order to receive the highest possible resolution.

The coil pairs (second magnetic means) 220', 220", 220''' are connected to current amplifiers 41, 51, 61, from which they receive their currents. The current amplifiers 41, 51, 61 are in turn in each case connected to an AC current source 42, 52, 62 which defines the temporal course of the currents Ix, Iy, Iz to be amplified. The AC current sources 42, 52, 62 are controlled by the control means 76.

The receiving coil (receiving means) is also shown schematically in FIG. 5. The signals induced in the receiving coil 230 are fed to a filter unit 71, by means of which the signals are filtered. The aim of this filtering is to separate measured values, which are caused by the magnetization in the examination area which is influenced by the change in position of the two part-regions (301, 302), from other, interfering signals. To this end, the filter unit 71 may be designed for example such that signals which have temporal frequencies that are smaller than the temporal frequencies with which the coil pairs 220', 220", 220''' are operated, or smaller than twice these temporal frequencies, do not pass the filter unit 71. The signals are then transmitted via an amplifier unit 72 to an analog/digital converter 73 (ADC). The digitalized signals produced by the analog/digital converter 73 are fed to an image processing unit (also called reconstruction means) 74, which reconstructs the spatial distribution of the magnetic particles from these signals and the respective position which the first part-region 301 of the first magnetic field in the examination area assumed during receipt of the respective signal and which the image processing unit 74 obtains from the control means 76. The reconstructed spatial distribution of the magnetic particles is finally transmitted via the control means 76 to the computer 12, which displays it on the monitor 13.

Figure 6:
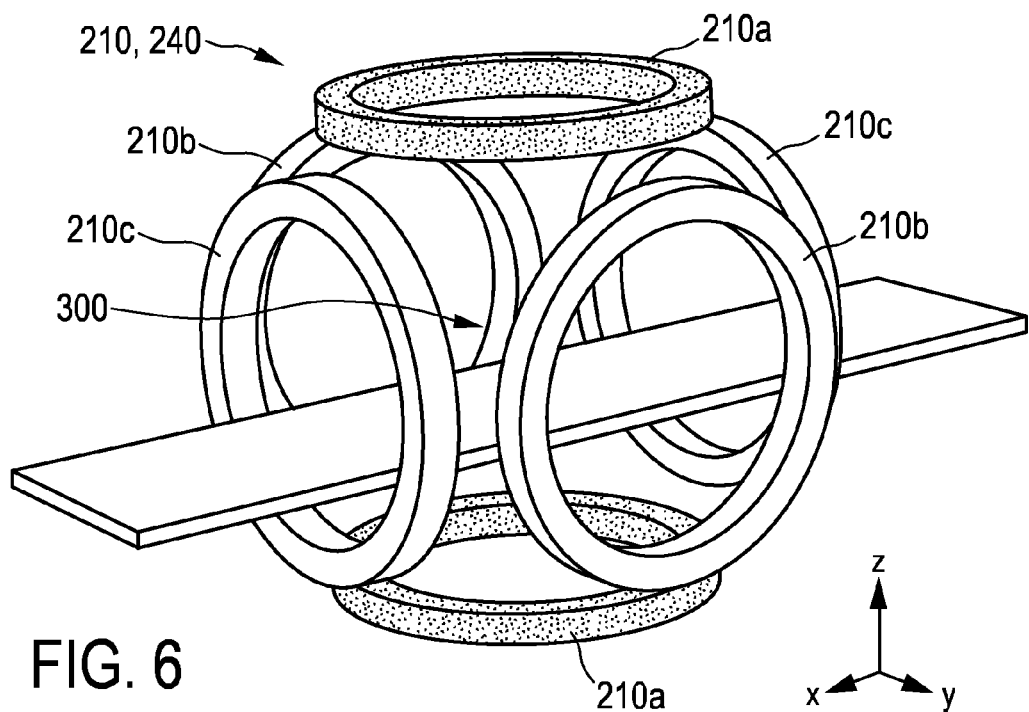
FIG. 6 shows an arrangement of the selection means according to an embodiment of the present invention.
Figure 8:
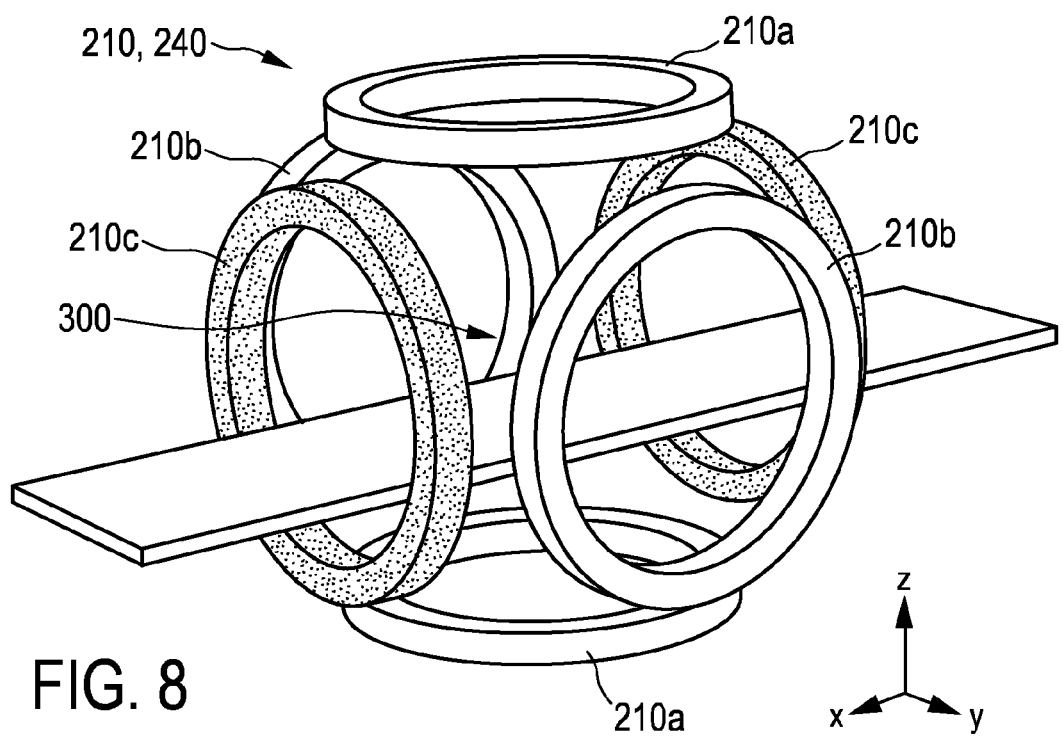
FIG. 8 shows a further arrangement of the selection means according to an embodiment of the present invention.

FIGS. 6 and 8 show arrangements of the selection means 210 according to an embodiment of the present invention. The selection means 210 are realized by three magnetic coil pairs 210a, 210b, 210c, surrounding the region of action 300, wherein the coil pairs are arranged perpendicular to each other, one for each spatial direction (x, y, z). Depending on the desired direction of maximum resolution, an overlaid current is overlaid to at least one of the coil pairs 210a, 210b, 210c, wherein the overlaid current of opposed coils of a coil pair is oppositely oriented.

Figure 7A:
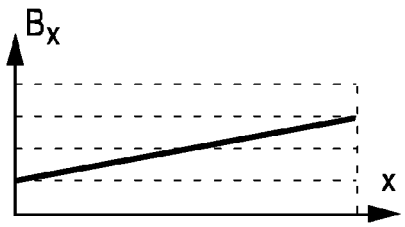
FIGS. 7a, 7b and 7c show the diagrams with the respective spatial magnetization gradients according to the embodiment shown in FIG. 6.
Figure 7B:
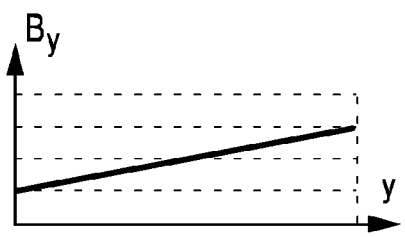
Figure 7C:
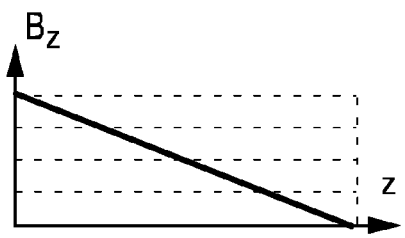
Figure 9A:
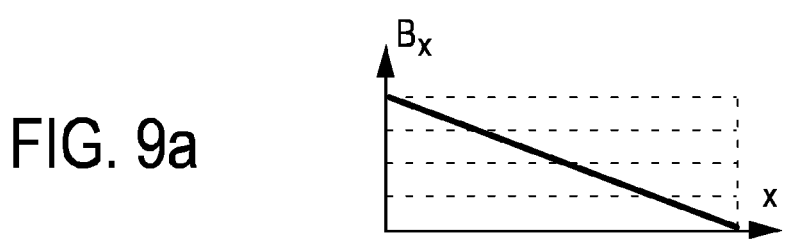
FIGS. 9a, 9b and 9c show the diagrams with the respective spatial magnetization gradients according to the embodiment shown in FIG. 8.
Figure 9B:
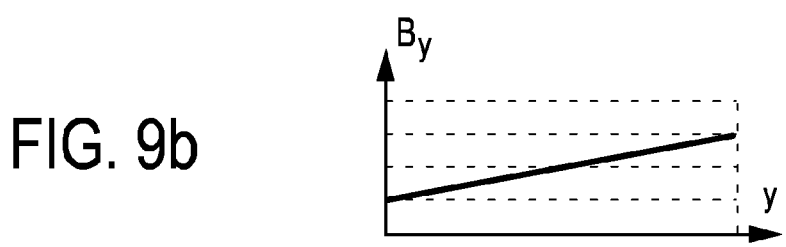
Figure 9C:
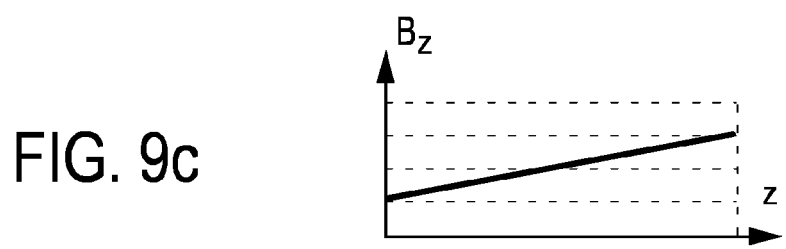

If, for example, the most critical direction, where the highest imaging resolution is needed, is in the z-direction, the overlaid current is applied to the coil pair 210a generating the z-fraction of the selection field 211 (see FIG. 6). As it can be seen by comparing FIGS. 7a-7c, the gradient, and thus, the imaging resolution is in this case twice as large in the z-direction than in the x- and y-direction. If, on the other hand, the most critical direction is the x-direction, the overlaid current is applied to the coil pair 210c generating the x-fraction of the selection field 211 (see FIG. 8). In this case, the gradient strength is twice as large in the x-direction compared to the y- and z-direction (see FIGS. 9a-9c).

Even though not especially illustrated here, it is obvious that the selection field 211 can also be directed in the y-direction by applying the overlaid current to the coil pair 210c. It also has to be noted that the direction of the highest resolution can be directed to any arbitrary user-defined direction by distributing the overlaid current over these coil pairs which generate the desired spatial fractions of the magnetic selection field 211. Thus, by providing only three coil pairs, the direction of the highest gradient can be varied to all possible directions within the region of action 300. The overall field and/or the overall gradient strength of the selection field 210 are thereby not changed. Thus, a higher resolution is received in any arbitrary direction without depositing additional energy to the examination object 350.

Furthermore, it has to be noted that the embodiments shown in FIGS. 6 and 8 are only exemplary and that the selection field generating means can also be provided by spherical coils or an arrangement of even more than three 3 coil pairs. It is clear that instead of distributing the overlaid current over different coil pairs, if a direction is desired deviating from the three principal spatial directions, the coil pairs can also be mechanically moved, turned and/or rotated.

In the embodiment shown in FIGS. 6 and 8 focus means 240 are furthermore provided for changing the position in space of the region of action 300. The operating range, in which magnetic particles can be influenced and/or detected, is therefore substantially enlarged so that for example longer blood vessels can easily be examined with the arrangement according to the present invention. In the shown embodiment the selection means 210 and the focus means 240 are combined. This is possible by designing larger coils which can concurrently generate the selection field 211 and the focus field.

Figure 10:
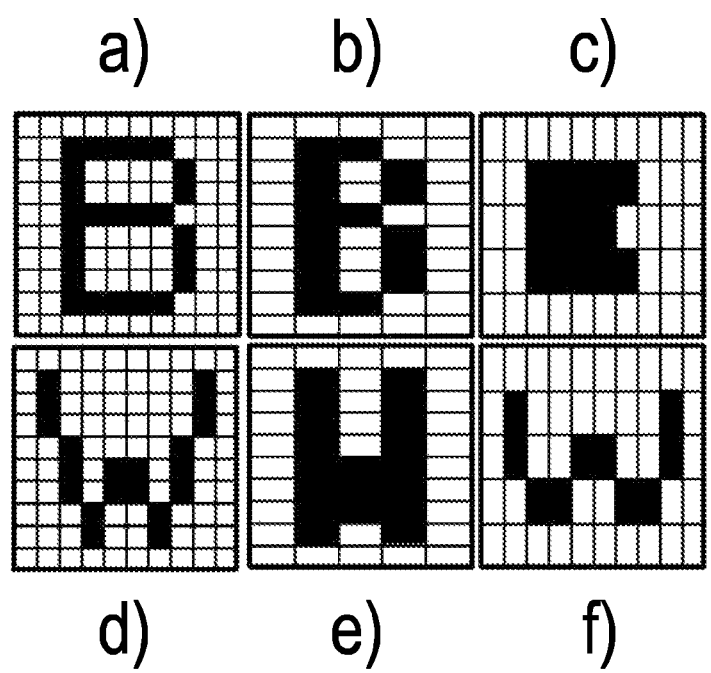
FIG. 10 shows examples of images produced by an arrangement according to the present invention.

FIG. 10 shows further examples concerning the principle explained above to illustrate the importance for adapting the gradient direction according to the most critical spatial direction. This is demonstrated by imaging the letters "B" and "W". Six images a)-f) are provided in FIG. 10: image a) and d) have been imaged with an isotropic imaging system, images b) and e) have been imaged with the system according to the present invention with the high-resolution direction in the vertical direction, and images c) and f) have been imaged with the system according to the present invention with the high-resolution direction in the horizontal direction.

While the letter "B" can clearly be imaged, if the high-resolution is aligned to the vertical direction, the letter "W" cannot. In contrast to that, the letter "B" cannot be imaged if the high-resolution is aligned along the horizontal direction, while the letter "W" can clearly be imaged. This clearly points out the importance and the advantage of the high-resolution adaptation according to the present invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An arrangement for at least one of spatially distributing and detecting magnetic particles in a region of action having a first sub-zone and a second sub-zone, comprising:
    selection means having three magnetic selection field generation means defining the region of action, one for each main spatial direction, each magnetic selection field generation means generating a selection field component of a static magnetic gradient field having a pattern in space of a magnetic field strength such that the first sub-zone having a low magnetic field strength and the second sub-zone having a higher magnetic field strength are formed in the region of action,
    drive means changing a position in space of the first sub-zone and the second sub-zone in the region of action by a magnetic drive field so that a magnetization of the magnetic particles changes locally, and
    control means controlling the three magnetic selection field generation means of said selection means to individually set the gradient strength of the selection field components generated by said three magnetic selection field generation means thereby setting a gradient strength and a direction of the gradient of the static magnetic gradient field.

2. An arrangement according to claim 1, characterized in that each magnetic selection field generation means includes a pair of opposed coils provided with identically oriented selection currents wherein the gradient strength of at least one of the selection field components is set by overlaying an overlaid current to at least one of the pairs of opposed coils with the overlaid current of opposed coils being oppositely oriented.

3. An arrangement according to claim 1, characterized in that each magnetic selection field generation means includes a pair of opposed permanent magnets wherein the gradient strength of at least one of the selection field components is set by mechanically moving at least one of the pairs of opposed permanent magnets.

4. An arrangement according to claim 3, wherein the moving is rotating.

5. An arrangement according to claim 1, further comprising:
    focus means changing the position in space of the region of action.

6. An arrangement according to claim 1, characterized in that the control means controls the magnetic selection field generation means of said selection means such that the sum of a field strength and the sum of the gradient strength of all three selection field components is maintained at a predefined fixed level.

7. An arrangement according to claim 1, further comprising:
    receiving means for acquiring detection signals, which detection signals depend on the magnetization of the magnetic particles in the region of action, which magnetization of the magnetic particles changes with the change in the position in space of the first sub-zone and the second sub-zone.

* * * * *